US009095252B2

(12) United States Patent
Popovic (10) Patent No.: US 9,095,252 B2
(45) Date of Patent: Aug. 4, 2015

(54) IMAGE INTEGRATION BASED REGISTRATION AND NAVIGATION FOR ENDOSCOPIC SURGERY

(75) Inventor: Aleksandra Popovic, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 378 days.

(21) Appl. No.: 13/521,284

(22) PCT Filed: Dec. 6, 2010

(86) PCT No.: PCT/IB2010/055606
§ 371 (c)(1),
(2), (4) Date: Jul. 30, 2012

(87) PCT Pub. No.: WO2011/086431
PCT Pub. Date: Jul. 21, 2011

(65) Prior Publication Data
US 2012/0294498 A1 Nov. 22, 2012

Related U.S. Application Data

(60) Provisional application No. 61/294,502, filed on Jan. 13, 2010.

(51) Int. Cl.
G06K 9/00 (2006.01)
G06K 9/32 (2006.01)
A61B 1/00 (2006.01)
(Continued)

(52) U.S. Cl.
CPC ........... *A61B 1/0005* (2013.01); *A61B 19/5244* (2013.01); *G06T 7/004* (2013.01); *A61B 1/042* (2013.01); *A61B 19/5212* (2013.01); *A61B 2019/505* (2013.01); *A61B 2019/5238* (2013.01);
(Continued)

(58) Field of Classification Search
None
See application file for complete search history.

(56) References Cited

U.S. PATENT DOCUMENTS 6,036,637 A 3/2000 Kudo
7,555,331 B2 6/2009 Viswanathan
(Continued)

FOREIGN PATENT DOCUMENTS

DE 102006041055 3/2008
WO WO2008103383 8/2008
WO WO2009045827 4/2009

OTHER PUBLICATIONS

C. Hu, et al., "A System for the Registration of Arthroscopic Images to Magnetic Resonance Images of the Knee: For Improved Virtual Knee Arthroscopy", Proc. SPIE, vol. 7261, 726119 (2009); Conference on Medical Imaging 2009: Visualization, Image-Guided Procedures, and modeling, Lake Buena Vista, FL, USA.

*Primary Examiner* — Matthew Bella
*Assistant Examiner* — Jose M Torres (57) ABSTRACT

A real-time tracking of surgical tools relative to a pre-operative surgical plan and intra-operative images involves an image-based registration and tool tracking registration. The image-based registration implements an integration of a plurality of images of an anatomical region of a body including a pre-operative scan image (31) (e.g., a 3D CT/MRI image), an intra-operative fluoroscopic image (42) (e.g., an 2D X-ray image) and an intra-operative endoscopic image (23) (e.g., an 2D arthroscopic image). The tool tracking registration implements a representation within the pre-operative scan image (31) and/or the intra-operative fluoroscopic image (42) of a tracking of one or more surgical tools within the intra-operative endoscopic image (23).

20 Claims, 6 Drawing Sheets

(51) Int. Cl.
*G06T 7/00* (2006.01)
*A61B 1/04* (2006.01)
*A61B 19/00* (2006.01)

(52) U.S. Cl.
CPC . *A61B 2019/5265* (2013.01); *A61B 2019/5289* (2013.01)

(56) References Cited

U.S. PATENT DOCUMENTS

| | | | |
|---|---|---|---|
| 7,824,328 | B2 * | 11/2010 | Gattani et al. ............... 600/117 |
| 2008/0097155 | A1 | 4/2008 | Gattani et al. |
| 2008/0207997 | A1 | 8/2008 | Higgins et al. |
| 2009/0080737 | A1 | 3/2009 | Battle et al. |
| 2009/0088634 | A1 * | 4/2009 | Zhao et al. ................. 600/427 |
| 2009/0103791 | A1 * | 4/2009 | Suri et al. .................. 382/131 |
| 2010/0172559 | A1 * | 7/2010 | Kumar et al. ............... 382/131 |

* cited by examiner

IMAGE INTEGRATION BASED REGISTRATION AND NAVIGATION FOR ENDOSCOPIC SURGERY

The present invention generally relates to a real-time tracking of surgical tools within an anatomical region of a body relative to a pre-operative plan and intra-operative images. The present invention specifically relates to an integration of pre-operative scan images, intra-operative fluoroscopic images and intra-operative endoscopic images for the real-time tracking and localization of the surgical tools.

Minimally invasive endoscopic surgery is a surgical procedure in which a rigid or flexible endoscope is introduced into a patient's body through a natural orifice or a small incision in the skin (i.e., a port). Additional surgical tools are introduced into the patient's body through similar ports with the endoscope being used to provide a visual feedback to a surgeon of the surgical tools as related to the surgical site.

Figure 1:
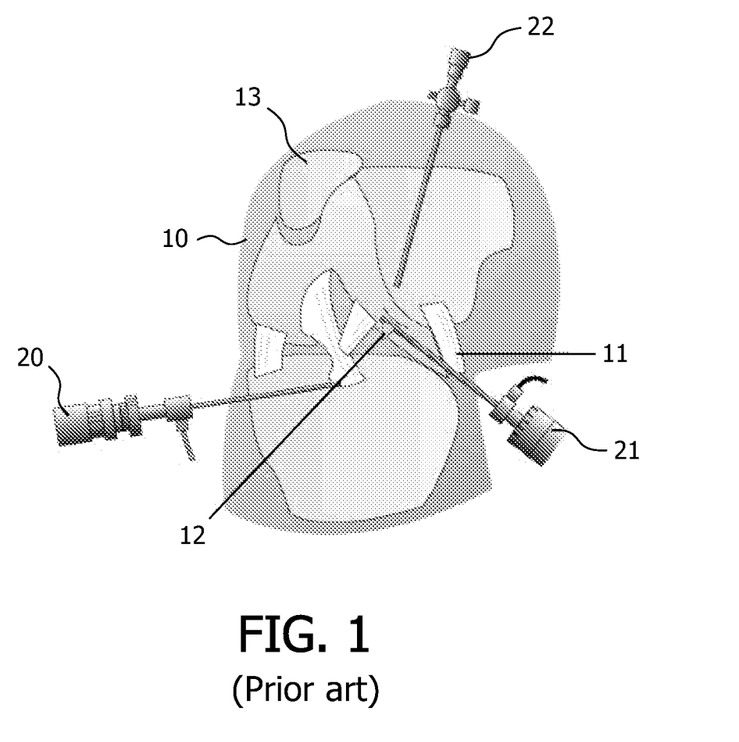
FIG. 1 illustrates a schematic representation of an ACL arthroscopic surgery as known in the art.

For example, FIG. 1 illustrates a schematic representation of an anterior cruciate ligament ("ACL") arthroscopic surgery of a knee 10, which is shown having an ACL 11, a cartilage 12 and a kneecap 13. The arthroscopic surgery involves a pre-operative phase and an intra-operative phase.

The pre-operative phase involves a three-dimensional ("3D") scan imaging of knee 10 (e.g., a CT image, a MRI image, an ultrasound image, an X-ray image, etc.) for diagnostic evaluation of knee 10 and for planning the ACL arthroscopic surgery of knee 10.

The intra-operative phase involves an introduction of an arthroscope 20 (i.e., an endoscope for joints) through a port in an anterior area of knee 10 whereby arthroscope 20 may be moved and/or pivoted to acquire real-time images of various regions of knee 10, in particular the ACL 11 and a damaged area of cartilage 12. Additionally, an irrigating instrument 22 is introduced through a port in a posterior area of knee 10, and various surgical instruments like a trimming instrument 21 are introduced through a port in the anterior area of knee 10 at an angle perpendicular to a viewing angle of arthroscope 20 to facilitate visualization of the surgical site for damaged cartilage 12.

Prior to the present invention, there were two main approaches for tracking positions and orientation of surgical tools 20-22.

Figure 2:
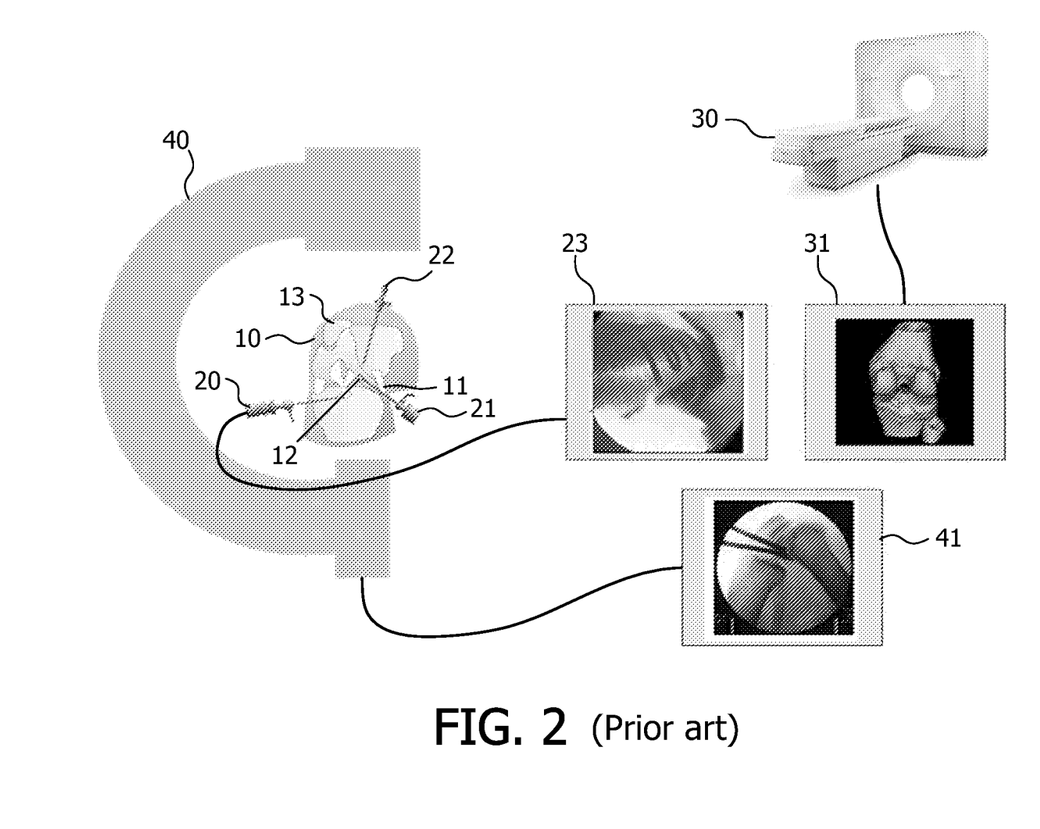
FIG. 2 illustrates an exemplary ACL arthroscopic surgery without surgical navigation as known in the art.

The first approach is a free-hand technique without navigation whereby a surgeon views the surgical field through three (3) different modalities. For example, as shown in FIG. 2, a CT scanner 30 is used to acquire a pre-operative CT scan image 31 for diagnostic and surgical planning purposes. An X-ray device 40 is used to acquire one or more intra-operative two-dimensional ("2D") fluoroscopic images, such as exemplary image 41, for viewing a position and orientation of one or more surgical tools 20-22 relative to knee 10. And, arthroscope 20 is used to continually acquire intra-operative arthroscopic images, such as exemplary image 23, for viewing the surgical site of knee 10.

A surgeon may view the images on different display screens, or one the same display screen. In either case, this approach fails to establish a relationship between the images that facilitates a tracking of the positions and orientations of one or more of the surgical tools 20-22 relative to knee 10, in particularly the surgical site of knee 10.

Figure 3:
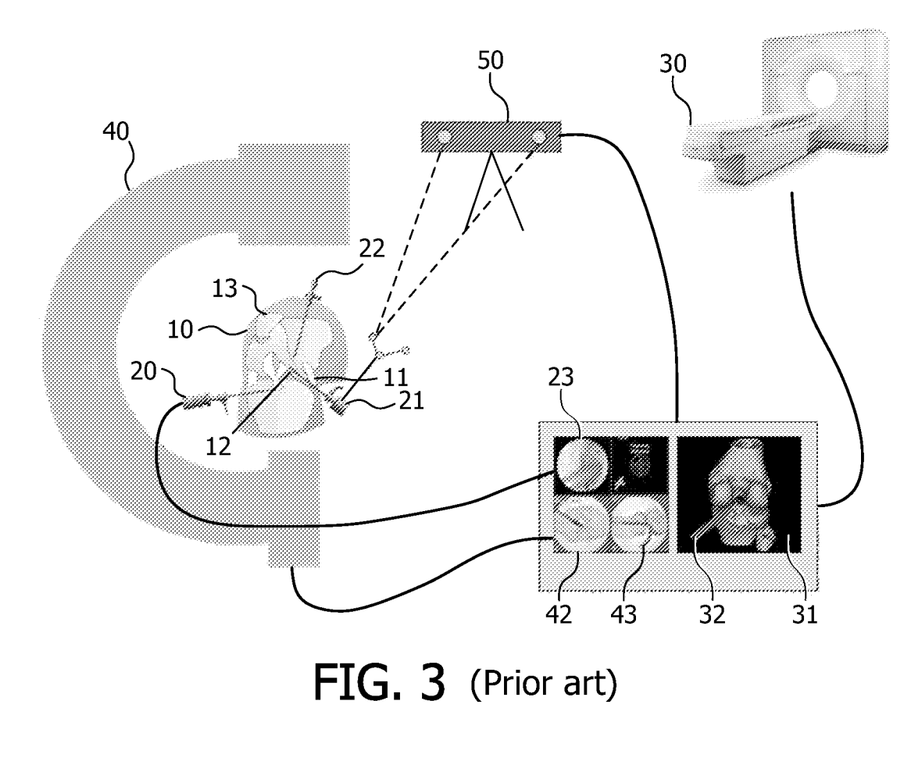
FIG. 3 illustrates an exemplary ACL arthroscopic surgery with surgical navigation as known in the art.

The second approach is a navigation-based surgery that solves the problem of tracking the positions and orientations of one or more of the surgical tools 20-22 relative to knee 10 by the use of external position tracking systems. For example, FIG. 3 illustrates an optical tracking system 50 for tracking the positions and orientations of trimming instrument 21 in a coordinate system of a tracking camera of system 50 whereby a patient registration procedure must be performed in order to present trimming instrument 21 as overlays in the scan image and the fluoroscopic image(s), such as exemplary overlays 32 and 43 in respective coordinate systems of scan image 31 and fluoroscopic images 42. The registration may use fiducial markers visible on the fluoroscopic images 42 that are attached to the patient's skin or bone, and palpated with the trimming instrument 21. Alternatively, a marker-less registration involving CT scan image 31 and fluoroscopic images 42 may be performed.

The second approach as shown in FIG. 3 provides a surgeon with real-time feedback of positions and orientations of trimming instrument 21 relative to knee 10 and a pre-operative plan. However, the use of optical tracking system 50 or an alternative external tracking system (e.g., an electromagnetic tracking system) increases the time of the surgical procedure via the patient registration, is unable to track all of the tools 20-22, and may add physical movement limitations to the surgeon (e.g., a line-of-sight between system 50 and trimming instrument 21 must be maintained at all times).

The present invention provides real-time tracking of surgical tools relative to a pre-perative surgical plan and intra-operative images that involves an image-based registration and a tool tracking. The image-based registration implements an integration of a plurality of images of an anatomical region of a body including a pre-operative scan image (e.g., a 3D CT/MRI image), an intra-operative fluoroscopic image (e.g., a 2D X-ray image) and an intra-operative endoscopic image (e.g., an 2D arthroscopic image). The tool tracking implements a representation within the pre-operative scan image and/or the intra-operative fluoroscopic image of a tracking of one or more surgical tools via the intra-operative endoscopic image.

One form of the present invention is a surgical navigation system for integrating a plurality of images of an anatomical region of a body including a pre-operative scan image (e.g., a 3D CT/MRI image), an intra-operative fluoroscopic image (e.g., a 2D X-ray image) and an intra-operative endoscopic image (e.g., a 2D arthroscopic image). The surgical navigation system includes an image integrator and a tool tracker. In operation, the image integrator generates an integrated image matrix including an integration (e.g., a matrix multiplication) of a fluoroscopic image matrix and an endoscopic image matrix, wherein the fluoroscopic image matrix includes a transformation between the intra-operative fluoroscopic image and the pre-operative scan image, and wherein the endoscopic image matrix includes a transformation between the pre-operative scan image and the intra-operative endoscopic image. In turn, the tool tracker generates an integrated tracking matrix, wherein the integrated tracking matrix includes an integration (e.g., a matrix multiplication) of the integrated image matrix and an endoscopic tracking matrix, and wherein the endoscopic tracking matrix represents a tracking of a surgical tool within the intra-operative endoscopic image.

The tool track may further or alternatively generate a scan tracking matrix, wherein the scan tracking matrix includes an integration (e.g., a matrix multiplication) of the endoscopic image matrix and the endoscopic tracking matrix.

For purposes of the present invention, the term "generating" as used herein is broadly defined to encompass any technique presently or subsequently known in the art for creating, supplying, furnishing, obtaining, producing, forming, developing, evolving, modifying, transforming, altering or otherwise making available information (e.g., data, text, images, voice and video) for computer processing and memory storage/retrieval purposes, particularly image datasets and video frames, and the term "registration" as used herein is broadly defined to encompass any technique presently or subsequently known in the art for transforming different sets of image data into one coordinate system.

Additionally, the term "pre-operative" as used herein is broadly defined to describe any activity occurring or related to a period or preparations before an endoscopic application (e.g., path planning for an endoscope) and the term "intra-operative" as used herein is broadly defined to describe as any activity occurring, carried out, or encountered in the course of an endoscopic application (e.g., operating the endoscope in accordance with the planned path). Examples of an endoscopic application include, but are not limited to, an arthroscopy, a bronchoscopy, a colonscopy, a laparoscopy, a brain endoscopy, and an endoscopic cardiac surgery. Examples of an endoscopic cardiac surgery include, but are not limited to, endoscopic coronary artery bypass, endoscopic mitral and aortic valve repair and replacement.

In most cases, the pre-operative activities and intra-operative activities will occur during distinctly separate time periods. Nonetheless, the present invention encompasses cases involving an overlap to any degree of pre-operative and intra-operative time periods.

Furthermore, the term "endoscopic" is broadly defined herein as a characterization of images acquired by any type of endoscope having the ability to image from inside a body, and the term "fluoroscopic" is broadly defined herein as a characterization of images acquired by any type of fluoroscope having the ability to provide real-time images of the internal structures of a body. Examples of an endoscope for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, or miniaturized (e.g. CCD based) imaging systems. Examples of fluoroscope for purposes of the present invention include, but are not limited to, an X-ray imaging system.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 4:
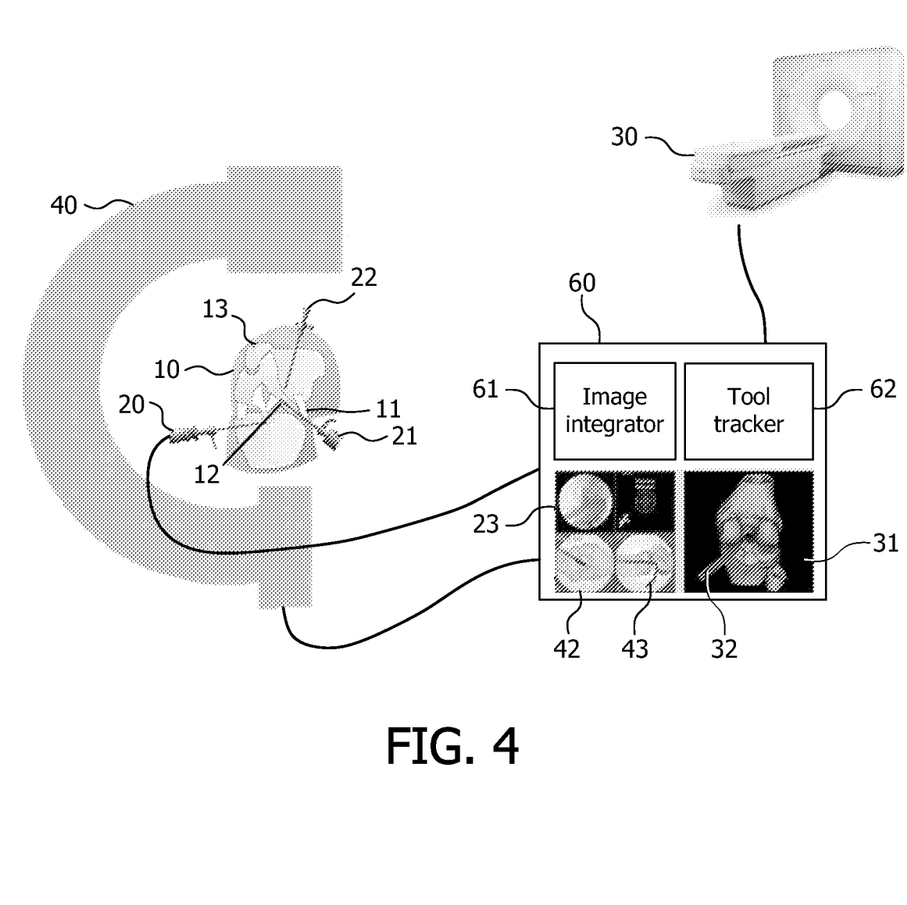
FIG. 4 illustrates an exemplary ACL arthroscopic surgery with surgical navigation in accordance with an exemplary embodiment of a surgical navigation system of the present invention.

Referring to FIG. 4, a surgical navigation system 60 of the present invention for real-time tracking of surgical tools relative to a pre-operative surgical plan and intra-operative images that involves an image-based registration and a tool tracking. To this end, system 60 includes an image integrator 61, a tool tracker 62 and a display device for illustrating images 23, 31, 43. Image integrator 61 is broadly defined herein as any device structurally configured for implementing the image-based registration involving an integration of a plurality of images of an anatomical region of a body including a pre-operative scan image (e.g., a 3D CT/MRI image), an intra-operative fluoroscopic image (e.g., a 2D X-ray image) and an intra-operative endoscopic image (e.g., an 2D arthroscopic image). Tool tracker 62 is broadly defined herein as any device structurally configured for implementing the tool tracking involving on overlay of a surgical tool within the pre-operative scan image and/or the intra-operative fluoroscopic image as a representation of tracking of the surgical tool within the intra-operative endoscopic image. The display device is broadly defined herein as any device structurally configured for displaying images and tracked surgical tools under any suitable technique, such as, for example, an augmented virtual visualization of images and tracked surgical tools.

Figure 5:
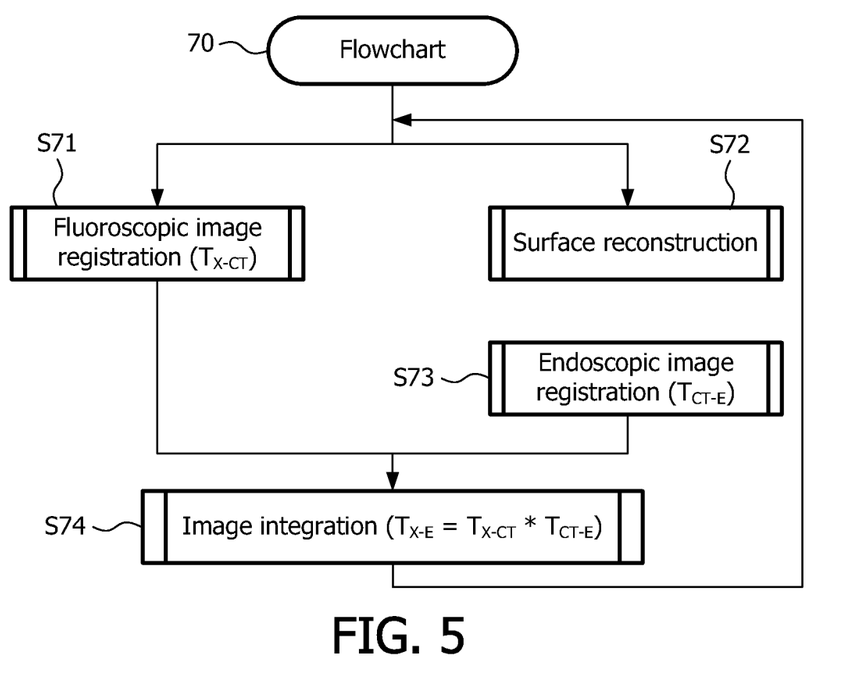
FIG. 5 illustrates a flowchart representative of an exemplary embodiment of an image integration method in accordance with the present invention.

FIG. 5 illustrates a flowchart 70 representative of an image integration method executed by image integrator 61. Referring to FIG. 5, flowchart 70 has a fluoroscopic path and an endoscopic path with both paths leading to an image integration stage S74. The fluoroscopic path includes a stage S71 of flowchart 70 encompassing a fluoroscopic image registration of an intra-operative fluoroscopic image (e.g., image 41 of FIG. 4) and a pre-operative scan image (e.g., image 31 of FIG. 4). In one embodiment of stage S71, the fluoroscopic image registration involves a rigid spatial transformation as known in the art of a 2D intra-operative fluoroscopic image as a target image to align with a 3D pre-operative scan image as a reference image to thereby generate a fluoroscopic image matrix $T_{X\text{-}CT}$ ($T_{CT\text{-}X} = T^{-1}_{X\text{-}CT}$, where $^{-1}$ represents matrix inversion known in art). Alternatively, the fluoroscopic image registration may involve a rigid spatial transformation as known in the art of the 3D pre-operative scan image as the target image to align with the 2D intra-operative fluoroscopic image as the reference image to thereby generate the fluoroscopic image matrix ($T_{CT\text{-}X}$).

Stage S71 is executed by image integrator 60 upon a generation of each new image frame via a fluoroscope (e.g., X-ray system 40 of FIG. 4), which is on a as needed basis as determined by a surgeon during a surgical procedure.

The endoscopic path includes a stage S72 and a stage S73 of flowchart 70. Stage S72 encompasses a surface reconstruction of an object within an intra-operative endoscopic image (e.g., image 23 of FIG. 4). In an exemplary embodiment of stage S72 for stereo endoscope (e.g., arthroscope with two cameras taking two images at the same time), any stereoscopic 3D reconstruction method as known in the art may be used.

In an exemplary embodiment of stage S72 for a monocular endoscope (e.g., a single camera arthroscope taking images), any photogrammetric reconstruction technique as known in the art may be used. For example, given the velocity of the monocular endoscope, a depth map may be extracted from an optical flow. Specifically, the optical flow is a vector field representing motion of every point or feature within an image time series whereby a point on the optical flow that is not moving in consecutive slices is called a focus of expansion ("FOE"). The endoscope's optical axis is aligned with its movement, thus the FOE is aligned with the endoscope's movement. Depth information (Z) may be extracted in accordance with Z=v*D/V by knowing a distance (D) of every point or feature from the FOE, an amplitude of optical flow in every point (V) and a velocity of the endoscope (v). The X and Y position of the endoscope may be computed from intrinsic camera parameters (e.g., focal point, etc.).

As would be appreciated by those having ordinary skill in the art, the endoscope is pivoted for surface reconstruction purposes without the use of optical cues, and alternatively, the endoscope does not have to be pivoted for surface reconstruction purposes with the use of optical cues.

Stage S73 encompasses an endoscopic image registration of a pre-operative scan image (e.g., image 31 of FIG. 4) and a surface reconstruction within an intra-operative endoscopic image (e.g., image 23 of FIG. 4). In one exemplary embodiment of stage S73, the endoscopic image registration involves a rigid spatial transformation as known in the art of the surface reconstruction within the intra-operative endoscopic image as a target image to align with a 3D pre-operative scan image as a reference image to thereby generate an endoscopic image matrix $T_{CT-E}$ ($T_{E-CT}=T^{-1}_{CT-E}$). Specifically, bone surface shown in the pre-operative scan image may be segmented using image thresholding at a defined characteristic Hounsfield unit (e.g., 175 HU) and an Iterative Closest Point (ICP) algorithm may be executed to transform the images. Alternatively, the endoscopic image registration involves a rigid spatial transformation as known in the art of the 3D pre-operative scan image as the target image to align with surface reconstruction within the intra-operative endoscopic image as the reference image to thereby generate the endoscopic image matrix $T_{E-CT}$.

Stage S73 is executed by image integrator 60 upon a generation of each new image frame via the endoscopic device(s) (e.g., arthroscope 40 of FIG. 4), which is on a continual basis during the surgical procedure.

Stage S74 encompasses an image integration of the fluoroscopic image matrix $T_{X-CT}$ of stage S71 and the endoscopic image matrix $T_{CT-E}$ of stage S73. In one exemplary embodiment of stage S74, the image integration includes a matrix multiplication as known in the art of the fluoroscopic image matrix $T_{X-CT}$ and endoscopic image matrix $T_{CT-E}$ to thereby yield an integrated image matrix $T_{X-E}$ ($T_{E-X}=T^{-1}_{X-E}$).

Flowchart 70 remains in a loop during the surgical procedure with stage S74 continually being updated via the endoscopic path S72 and S73 as integrated with the most current fluoroscopic image registration of stage S71.

Figure 6:
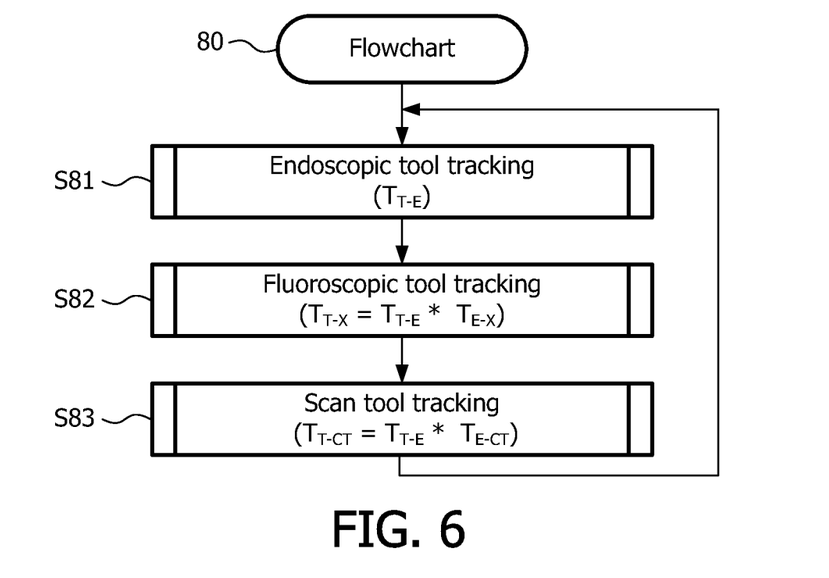
FIG. 6 illustrates a flowchart representative of an exemplary embodiment of a tool tracking method in accordance with the present invention.

FIG. 6 illustrates a flowchart 80 representative of a tool tracking method executed by tool tracker 62 (FIG. 4). Referring to FIG. 6, a stage S81 of flowchart 80 encompasses a tracking of a surgical tool within an intra-operative endoscopic image (e.g., image 23 of FIG. 4) and a generation of an endoscopic image matrix $T_{T-E}$ representing a position of a surgical tool (T) in the intra-operative endoscopic image (E) (e.g. endoscopic image matrix $T_{T-E}$ may be a transformation matrix showing the tool tip in the translation component and the tool orientation in the rotation component). In one exemplary embodiment of stage S81, tool tracker 61 executes a photogrammetric tracking technique as known in the art. Specifically, a surgical tool usually has a high contrast within an endoscopic image compared to the background of the endoscopic image (e.g., bone). Thus, it is possible to detect the position of the surgical tool within the endoscopic image by segmenting the image using thresholding on three (3) color channels. Alternatively, a tip of the surgical tool may be painted with a distinct color rarely observable within a body (e.g., green), which would simply the segmentation via a green color channel. In either case, once the surgical tool is detected via the segmentation of the endoscopic image, a depth estimation technique a previously described herein may be used to estimate the depth of the tool relative to the endoscopic frame.

Stage S82 of flowchart 80 encompasses a tracking of the surgical tool within the intra-operative fluoroscopic image via an integration of endoscopic tracking matrix $T_{T-E}$ ($T_{E-T}=T^{-1}_{T-E}$) and integrated image matrix $T_{X-E}$. In one exemplary embodiment of stage S82, the integration includes a matrix multiplication as known in the art of the endoscopic tracking matrix $T_{T-E}$ and an inverse of integrated image matrix $T_{X-E}$ to thereby yield a fluoroscopic tracking matrix $T_{T-X}$ ($T_{X-T}=T^{-1}_{T-X}$).

Stage S83 of flowchart 80 encompasses a tracking of the surgical tool within the pre-operative scan image via an integration of endoscopic tracking matrix $T_{T-E}$ and the endoscopic image matrix $T_{CT-E}$. In one exemplary embodiment of stage S83, the integration includes a matrix multiplication as known in the art of the endoscopic tracking matrix $T_{T-E}$ and an inverse of endoscopic image matrix $T_{CT-E}$ to thereby yield a scan tracking matrix $T_{T-CT}$ ($T_{CT-T}=T^{-1}_{T-CT}$).

The results of stages S82 and S83 are a display of real-time tracking of a surgical tool within a pre-operative scan image and an intra-operative fluoroscopic image, such as, for example, the tracking overlay 32 of pre-operative scan image 31 as shown in FIG. 4 and the tracking overlay 43 of intra-operative fluoroscopic image 42 as shown in FIG. 4. This is accomplished without the need of an external imaging system (although one may be used to complement the endoscopic device) and a patient registration.

Figure 7:
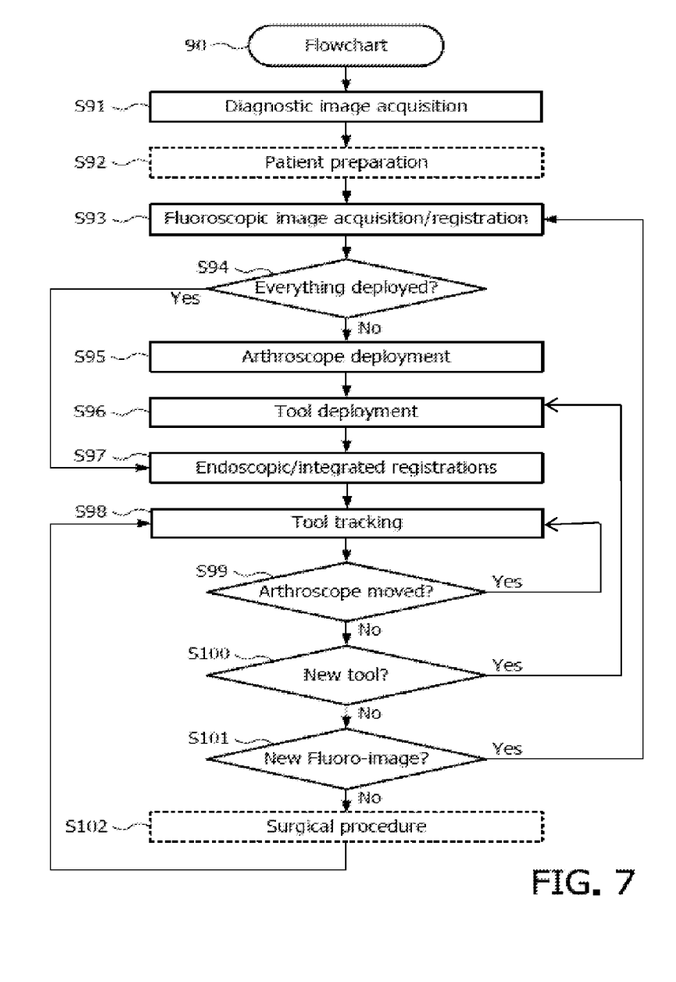
FIG. 7 illustrates a flowchart representative of an exemplary embodiment of a surgical navigation method in accordance with the present invention.

FIG. 7 illustrates a flowchart 90 representative of a surgical navigation method embodying flowchart 70 (FIG. 5) and flowchart 80 (FIG. 6) in the context of an ACL arthroscopic surgery.

Specifically, a stage S91 of flowchart 90 encompasses an acquisition of a pre-operative scan image (e.g., a 3D CT image, a 3D MRI image, a 3D X-ray image, a 3D fluoroscopic image, etc.). A stage S92 of flowchart 90 encompasses a preparation of the patient for ALC arthroscopic surgery. For example, the patient prep may include a grating of a tendon of the knee and a fixation of the knee for surgery. A stage S93 of flowchart 90 encompasses an acquisition of an intra-operative fluoroscopic image (e.g., a 2D X-ray image) and an execution of a fluoroscopic registration of stage S71 (FIG. 5).

A first pass through flowchart 90 involves stage S93 proceeding to stages S95-S98. Stage S95 encompasses a deployment of the arthroscope within the knee (e.g., arthroscope 20 of FIG. 4). Stage S96 encompasses a deployment of additional surgical tools within the knee (e.g., trimming instrument 21 and irrigating instrument 22 of FIG. 4). Stage S97 encompasses an acquisition of the intra-operative endoscopic image and an execution of an surface reconstruction of stage S72 (FIG. 5), an endoscopic registration of stage S73 (FIG. 5), and an image integration of stage S74 (FIG. 5). And, stage S98 encompasses a tracking of a surgical tool in accordance with flowchart 80 (FIG. 6).

Decision stages S99-S101 allow for a continual loop between a surgical procedure stage S102 and tool tracking stage S98 until (1) the arthroscope is being moved by the surgeon, which necessitates a return to stage S97, (2) a new surgical tool to be tracked is introduced by the surgeon within the knee, which necessitate a return to stage S96, or (3) the surgeon determines a need for a new fluoroscopic image, which necessitates a return to stage S93. Any return to stage S93 will proceed to stage S97 via a decision stage S94 if the arthroscope and tracked surgical tools are still being deployed.

In practice, those having ordinary skill in the art will appreciate how to implement flowchart 90 for other endoscopic applications.

While various embodiments of the present invention have been illustrated and described, it will be understood by those skilled in the art that the methods and the system as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention include all embodiments falling within the scope of the appended claims.

The invention claimed is:

1. A surgical navigation system (60) for integrating a plurality of images of an anatomical region of a body including a pre-operative scan image (31), an intra-operative fluoroscopic image (42) and an intra-operative endoscopic image (23), the surgical navigation system (60) comprising:
   an image integrator (61) operable to generate an integrated image matrix ($T_{X-E}$) including an integration of a fluoroscopic image matrix ($T_{X-CT}$) and an endoscopic image matrix ($T_{CT-E}$),
      wherein the fluoroscopic image matrix ($T_{X-CT}$) includes a transformation between the intra-operative fluoroscopic image (42) and the pre-operative scan image (31), and
      wherein the endoscopic image matrix ($T_{CT-E}$) includes a transformation between the pre-operative scan image (31) and the intra-operative endoscopic image (23); and
   a tool tracker (62) operable to generate an integrated tracking matrix ($T_{T-X}$) and a scan tracking matrix ($T_{T-CT}$),
      wherein the integrated tracking matrix ($T_{T-X}$) includes an integration of the integrated image matrix ($T_{X-E}$) and an endoscopic tracking matrix ($T_{T-E}$),
      wherein the scan tracking matrix ($T_{T-CT}$) includes an integration of the endoscopic image matrix ($T_{CT-E}$) and the endoscopic tracking matrix ($T_{T-E}$), and
      wherein the endoscopic tracking matrix ($T_{T-E}$) represents a tracking of a surgical tool (21) within the intra-operative endoscopic image (23).

2. The surgical navigation system (60) of claim 1, wherein the image integrator (61) is further operable to execute a photogrammetric reconstruction of a surface of an object within the intra-operative endoscopic image (23) as a basis for the transformation between the pre-operative scan image (31) and the intra-operative endoscopic image (23).

3. The surgical navigation system (60) of claim 1, wherein the integration of the fluoroscopic image matrix ($T_{X-CT}$) and the endoscopic image matrix ($T_{CT-E}$) includes an execution of a matrix multiplication involving the fluoroscopic image matrix ($T_{X-CT}$) and the endoscopic image matrix ($T_{CT-E}$).

4. The surgical navigation system (60) of claim 1, wherein the integration of the integrated image matrix ($T_{X-E}$) and an endoscopic tracking matrix ($T_{T-E}$) includes an execution of a matrix multiplication involving the integrated image matrix ($T_{X-E}$) and the endoscopic tracking matrix ($T_{T-E}$).

5. The surgical navigation system (60) of claim 1, wherein the integration of the endoscopic image matrix ($T_{CT-E}$) and the endoscopic tracking matrix ($T_{T-E}$) includes an execution of a matrix multiplication involving the endoscopic image matrix ($T_{CT-E}$) and the endoscopic tracking matrix ($T_{T-E}$).

6. The surgical navigation system (60) of claim 1, further comprising:
   a display device for displaying the intra-operative fluoroscopic image (42) having an overlay (43) of a surgical tool (21) as a function of the integrated tracking matrix ($T_{T-X}$).

7. The surgical navigation system (60) of claim 1, further comprising:
   a display device for displaying the pre-operative scan image (31) having an overlay (43) of a surgical tool (21) as a function of the scan tracking matrix ($T_{T-CT}$).

8. The surgical navigation system (60) of claim 1, wherein the tool tracker (62) is further operable to execute a photogrammetric tracking of the surgical tool (21) within the intra-operative endoscopic image (23).

9. The surgical navigation system (60) of claim 1, wherein the pre-operative scan image (31) is selected from a group consisting of a computed tomography image, magnetic resonance image, an ultrasound image and an X-ray image.

10. A surgical navigation system (60) for integrating a plurality of images of an anatomical region of a body including a pre-operative scan image (31), an intra-operative fluoroscopic image (42) and an intra-operative endoscopic image (23), the surgical navigation system (60) comprising:
    an image integrator (61) operable to generate an integrated image matrix ($T_{X-E}$) including an integration of a fluoroscopic image matrix ($T_{X-CT}$) and an endoscopic image matrix ($T_{CT-E}$),
       wherein the fluoroscopic image matrix ($T_{X-CT}$) includes a transformation between the intra-operative fluoroscopic image (42) and the pre-operative scan image (31), and
       wherein the endoscopic image matrix ($T_{CT-E}$) includes a transformation between the pre-operative scan image (31) and the intra-operative endoscopic image (23); and
    a tool tracker (62) operable to generate an integrated tracking matrix ($T_{T-X}$),
       wherein the integrated tracking matrix ($T_{T-X}$) includes an integration of the integrated image matrix ($T_{X-E}$) and an endoscopic tracking matrix ($T_{T-E}$), and
       wherein the endoscopic tracking matrix ($T_{T-E}$) represents a tracking of a surgical tool (21) within the intra-operative endoscopic image (23).

11. The surgical navigation system (60) of claim 10, the image integrator (61) is further operable to reconstruct a surface of an object within the intra-operative endoscopic image (23) as a basis for the transformation between the pre-operative scan image (31) and the intra-operative endoscopic image (23).

12. The surgical navigation system (60) of claim 10, wherein the integration of the fluoroscopic image matrix ($T_{X-CT}$) and the endoscopic image matrix ($T_{CT-E}$) includes an execution of a matrix multiplication involving the fluoroscopic image matrix ($T_{X-CT}$) and the endoscopic image matrix ($T_{CT-E}$).

13. The surgical navigation system (60) of claim 10, wherein the integration of the integrated image matrix ($T_{X-E}$) and an endoscopic tracking matrix ($T_{T-E}$) includes an execution of a matrix multiplication involving the integrated image matrix ($T_{X-E}$) and the endoscopic tracking matrix ($T_{T-E}$).

14. The surgical navigation system (60) of claim 10, further comprising:
a display device for displaying the intra-operative fluoroscopic image (42) having an overlay (43) of a surgical tool (21) as a function of the integrated tracking matrix ($T_{T-X}$).

15. The surgical navigation system (60) of claim 10, wherein the tool tracker (62) is further operable to execute a photogrammetric tracking of the surgical tool (21) within the intra-operative endoscopic image (23).

16. A surgical navigation method for integrating a plurality of images of an anatomical region of a body including a pre-operative scan image (31), an intra-operative fluoroscopic image (42) and an intra-operative endoscopic image (23), comprising:
generating an integrated image matrix ($T_{X-E}$) including an integration of a fluoroscopic image matrix ($T_{X-CT}$) and an endoscopic image matrix ($T_{CT-E}$),
wherein the fluoroscopic image matrix (T) includes a transformation between the intra-operative fluoroscopic image (42) and the pre-operative scan image (31), and
wherein the endoscopic image matrix ($T_{CT-E}$) includes a transformation between the pre-operative scan image (31) and the intra-operative endoscopic image (23); and
generating an integrated tracking matrix ($T_{T-X}$) and a scan tracking matrix ($T_{T-CT}$),
wherein the integrated tracking matrix ($T_{T-X}$) includes an integration of the integrated image matrix ($T_{X-E}$) and an endoscopic tracking matrix ($T_{T-E}$),
wherein the scan tracking matrix ($T_{T-CT}$) includes an integration of the endoscopic image matrix ($T_{CT-E}$) and the endoscopic tracking matrix ($T_{T-E}$), and
wherein the endoscopic tracking matrix ($T_{T-E}$) represents a tracking of a surgical tool (21) within the intra-operative endoscopic image (23).

17. The surgical navigation method of claim 16, wherein the integration of the fluoroscopic image matrix ($T_{X-CT}$) and the endoscopic image matrix ($T_{CT-E}$) includes an execution of a matrix multiplication involving the fluoroscopic image matrix ($T_{X-CT}$) and the endoscopic image matrix ($T_{CT-E}$).

18. The surgical navigation method of claim 16, wherein the integration of the integrated image matrix ($T_{X-E}$) and an endoscopic tracking matrix ($T_{T-E}$) includes an execution of a matrix multiplication involving the integrated image matrix ($T_{X-E}$) and the endoscopic tracking matrix ($T_{T-E}$).

19. The surgical navigation method of claim 16, wherein the integration of the endoscopic image matrix ($T_{CT-E}$) and the endoscopic tracking matrix ($T_{T-E}$) includes an execution of a matrix multiplication involving the endoscopic image matrix ($T_{CT-E}$) and the endoscopic tracking matrix ($T_{T-E}$).

20. The surgical navigation method of claim 16, further comprising: displaying the intra-operative fluoroscopic image (42) having an overlay (43) of a surgical tool (21) as a function of the integrated tracking matrix ($T_{T-X}$); and displaying the pre-operative scan image (31) having an overly (43) of a surgical tool (21) as a function of the scan tracking matrix ($T_{T-CT}$).

* * * * *